United States Patent
Turcott et al.

(10) Patent No.: US 6,792,310 B1
(45) Date of Patent: Sep. 14, 2004

(54) METHODS, SYSTEMS AND DEVICES FOR OPTIMIZING CARDIAC PACING PARAMETERS

(75) Inventors: Robert Turcott, Mountain View, CA (US); Casey O'Hara, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 504 days.

(21) Appl. No.: 09/759,395

(22) Filed: Jan. 12, 2001

(51) Int. Cl.[7] .............................. A61N 1/18; A61N 1/20
(52) U.S. Cl. ............................................ 607/27; 607/28
(58) Field of Search .............................. 607/9, 27, 28, 607/29, 23, 19, 20, 14; 128/419

(56) References Cited

U.S. PATENT DOCUMENTS

| | | | |
|---|---|---|---|
| 5,024,222 A | 6/1991 | Thacker | 128/419 PG |
| 5,168,869 A | 12/1992 | Chirife | 128/419 PG |
| 5,334,222 A | 8/1994 | Salo et al. | 607/17 |
| 5,487,752 A | 1/1996 | Salo et al. | 607/17 |
| 5,527,347 A | 6/1996 | Shelton et al. | 607/9 |
| 5,540,727 A | 7/1996 | Tockman et al. | 607/18 |
| 5,549,650 A | 8/1996 | Bornzin et al. | 607/24 |
| 5,554,177 A | 9/1996 | Kieval et al. | 607/17 |
| 5,626,620 A | 5/1997 | Kieval et al. | 607/9 |
| 5,700,283 A | 12/1997 | Salo | 607/17 |
| 5,800,471 A | 9/1998 | Baumann | 607/25 |
| 5,836,987 A | 11/1998 | Baumann et al. | 607/17 |
| 5,891,176 A | 4/1999 | Bornzin | 607/18 |
| 6,154,675 A | * 11/2000 | Juran et al. | 607/29 |
| 6,223,072 B1 | * 4/2001 | Mika et al. | 600/510 |
| 6,233,487 B1 | * 5/2001 | Mika et al. | 607/27 |
| 6,522,923 B1 | * 2/2003 | Turcott | 607/27 |

\* cited by examiner

*Primary Examiner*—Daniel Robinson
(74) *Attorney, Agent, or Firm*—Steven M. Mitchell

(57) ABSTRACT

Cardiac performance associated with a current set of N pacing parameters is improved by adjusting the cardiac pacing parameters until optimal or substantially optimal cardiac performance is achieved. The cardiac performance associated with the current set of N pacing parameters is determined. An incrementing step, a determining step, and a increment updating step, are repeated for i=1 to N, where i represents which of the N pacing parameter is being adjusted. The incrementing step includes incrementing an $i^{th}$ pacing parameter in the current set of N pacing parameters based on a corresponding $i^{th}$ increment value, to thereby produce an $i^{th}$ set of test pacing parameters. The determining step includes determining a cardiac performance associated with the $i^{th}$ set of test pacing parameters. The increment updating step includes updating the $i^{th}$ increment value based on the cardiac performance associated with the $i^{th}$ set of test pacing parameters. Finally, after all of the N increment values have been updated, the current set of N pacing parameters is updated based on the updated increment values. The updated current set of N pacing parameters should provide superior cardiac performance than the previous current set of N pacing parameters.

24 Claims, 9 Drawing Sheets

METHODS, SYSTEMS AND DEVICES FOR OPTIMIZING CARDIAC PACING PARAMETERS

BACKGROUND OF THE INVENTION

1. Field of the Invention

The present invention relates generally to implantable cardiac stimulation devices. The present invention more particularly relates to methods, systems and devices for adjusting cardiac pacing parameters to optimize pacing effectiveness.

2. Related Art

Implantable cardiac stimulation devices are well known in the art. Such devices may include, for example, implantable cardiac pacemakers and defibrillators either alone or combined in a common enclosure. The devices are generally implanted in a pectoral region of the chest beneath the skin of a patient within what is known as a subcutaneous pocket. The implantable devices generally function in association with one or more electrode carrying leads which are implanted within the heart. The electrodes are positioned within the heart for making electrical contact with the muscle tissue of their respective heart chamber. Conductors within the leads couple the electrodes to the device to enable the device to deliver the desired electrical therapy.

Traditionally, therapy delivery has been limited to the right side of the heart. However, new lead structures and methods have been produced and practiced for also delivering cardiac rhythm management therapy from or to the left heart. These lead structures and methods provide electrode electrical contact with the left atrium and left ventricle of the heart by lead implantation within the coronary sinus of the heart. As is well known, the coronary sinus passes closely adjacent the left atrium, extends into the great vein adjacent the left ventricle, and then continues adjacent the left ventricle towards the apex of the heart.

It has been demonstrated that electrodes placed in the coronary sinus and great vein may be used for left atrial pacing, left ventricular pacing, and cardioversion and defibrillation. These advancements enable implantable cardiac stimulation devices to address the needs of the wide patient population, from those that would benefit from right heart side pacing alone, to those that would benefit from left heart side pacing in conjunction with right heart side pacing (bi-chamber pacing), to those that would benefit from left heart side pacing alone.

The potential of multi-site pacing to improve the hemodynamic status (also referred to as cardiac performance) of select patient populations is well established in the research community. One area of active research is in determining optimal ventricular pacing configurations. For example, the results of one study suggest that optimal results are obtained by pacing on the side of the heart that has the conduction delay, so that left ventricular pacing give superior performance for patients with a left bundle branch block, while right ventricular pacing yields better results in patients with right bundle branch block. As illustrated by those who conducted this study, the problem is typically couched in terms of pacing mode, so that comparison is made among right ventricular pacing, left ventricular pacing, and simultaneous bi-ventricular pacing. Unfortunately, this approach considers only a small subset of the parameter space, and therefore carries the risk of missing altogether the optimal pacing configuration (also referred to as the optimum pacing parameters).

Thus, there exists the further challenge, with multi-site pacing, of identifying the optimal pacing configuration (i.e., determining optimal pacing parameters). This challenge is complicated by the fact that only a limited region of the left ventricle is accessible for pacing, particularly when access is obtained via the coronary venous system.

A further challenge in multi-site pacing is that the number of potential pacing parameter combinations increases rapidly as the number of sites paced increases, making it that much more difficult to determine optimal pacing parameters. This problem can be formulated in terms of an abstract mathematical space, where each dimension of the space represents an adjustable independent pacing parameter. For example, in dual-chamber pacing (e.g., right atrium and right ventricle pacing) there is a single independent parameter, the atrioventricular (AV) delay (assuming a fixed pacing rate), and cardiac performance is a function of this parameter. In three chamber pacing (e.g., right atrium, right ventricle and left ventricle) there are two independent parameters (AV delay and interventricular RV-LV delay), and thus a two dimensional parameter space (assuming a fixed pacing rate). This can be generalized to any number of dimensions. For example, the parameter space of a four-chamber pacemaker would have three dimensions (assuming a fixed pacing rate). If pacing rate is also being analyzed then another dimension is added.

Although not efficient, an exhaustive search of a one dimensional parameter space (e.g., when two-sites are being paced with a fixed pacing rate) is possible, as shown in U.S. Pat. No. 5,540,727. However, as the number of sites (and thus, parameters) increases, an exhaustive search of parameter space quickly become unworkable, as illustrated in the following table.

| # of sites | # of dimensions | # of test points per dimension | time average per test point | total time for an exhaustive search |
| --- | --- | --- | --- | --- |
| 2 | 1 | 10 | 5 sec | 50 sec |
| 3 | 2 | 10 | 5 sec | 8 min |
| 4 | 3 | 10 | 5 sec | 1 hour, 20 min |

Accordingly, there is a need for more efficient and effective methods, systems and devices for optimizing multiple pacing parameters.

An additional challenge in multi-site pacing is that the optimal pacing configuration is dependent on the physiologic state of the patient. In patients with Hypertrophic Obstructive Cardiomyopathy, for example, the degree of obstruction is dependent on posture. Thus, the optimal pacing configuration for an unseated, walking patient is likely to be different from what is optimal for a patient who is sedated and supine on the examination or operating table. Thus, there is a need for efficient and effective methods, systems and devices for optimizing pacing parameters, that can dynamically adapt to changes in the physiologic state of the patient.

Further, the optimal pacing configuration may change as the patient's myocardial state changes. Myocardial remodeling is associated with the progression or regression of heart failure. Such remodeling may depend on response to therapy, lifestyle changes, and age. As the heart remodels, the optimum sequence of activation may change. For example, in the acute phase of pacemaker implantation, left ventricular pacing may have been optimal for a given patient. Over weeks or months, the heart may remodel such that more synchronous bi-ventricular pacing becomes optimal. Thus, there is a need for efficient and effective methods, systems and devices for optimizing pacing parameters, that can dynamically adapt to changes in the myocardial state of the patient.

SUMMARY OF THE INVENTION

The present invention is directed towards methods, systems and devices for improving cardiac performance associated with a current set of pacing parameters by adjusting the cardiac pacing parameters until optimal or substantially optimal cardiac performance is acheived.

One embodiment of the present invention begins by determining cardiac performance associated with the current set of N pacing parameters, where N represents the number of parameters being optimized. This embodiment also includes repeating an incrementing step, a determining step, and an increment updating step, until an increment value associated with each of the N pacing parameters has been updated. The incrementing step includes incrementing an $i^{th}$ pacing parameter in the current set of N pacing parameters based on a corresponding $i^{th}$ increment value, to thereby produce an $i^{th}$ set of test pacing parameters. The determining step includes determining a cardiac performance associated with the $i^{th}$ set of test pacing parameters. In the increment updating step, the $i^{th}$ increment value is updated based on the cardiac performance associated with the $i^{th}$ set of test pacing parameters. Finally, after all of the N increment values have been updated, the current set of N pacing parameters is updated based on the updated increment values just determined. The updated current set of N pacing parameters should provide superior cardiac performance as compared to the previous current set of N pacing parameters.

The increment updating step can include updating the $i^{th}$ increment value based on the difference between the cardiac performance associated with the current set of N pacing parameters and the cardiac performance associated with the $i^{th}$ set of test pacing parameters, and based on the $i^{th}$ increment value's most recent value. This can cause the current set of N cardiac pacing parameters to approach an optimum set of pacing parameters by amounts proportional to the slope of the cardiac function.

The above discussed steps can be repeated indefinitely. Alternatively, the above discussed steps can be repeated until each of the updated increment values determined is less than a predetermined threshold value. This will give confidence that the most current set of N cardiac pacing parameters is close to an optimum set of pacing parameters.

In an alternative embodiment, the above discussed embodiment is modified such that the current set of N pacing parameters is immediately updated after an increment value has been updated.

In still other embodiments of the present invention, random sets of test pacing parameters are used to determine optimum or substantially optimum cardiac pacing parameters. This is accomplished by determining cardiac performance associated with a current set of N pacing parameters. Next, a random test set of N pacing parameters is determined. The cardiac performance associated with the test set of N pacing parameters is then determined. The current set of N pacing parameters is replaced with the test set of pacing parameters if the cardiac performance associated with the test set of pacing parameters is greater than the cardiac performance associated with the current set of N pacing parameters. These steps can be repeated indefinitely. Alternatively, the above discussed steps can be repeated, until, a predetermined number of consecutive times the cardiac performance associated with the test set of pacing parameters is not greater than the cardiac performance associated with the current set of N pacing parameters. This will provide confidence that substantially optimal pacing parameters have been found.

It is possible that sudden shifts in pacing parameters could have deleterious effects on patients. Accordingly, in another embodiment of the present invention, random searching is limited to a small range around the currently best known pacing parameters.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE INVENTION

The following description is of the best modes presently contemplated for practicing the invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

Exemplary Stimulation Device

Figure 1:
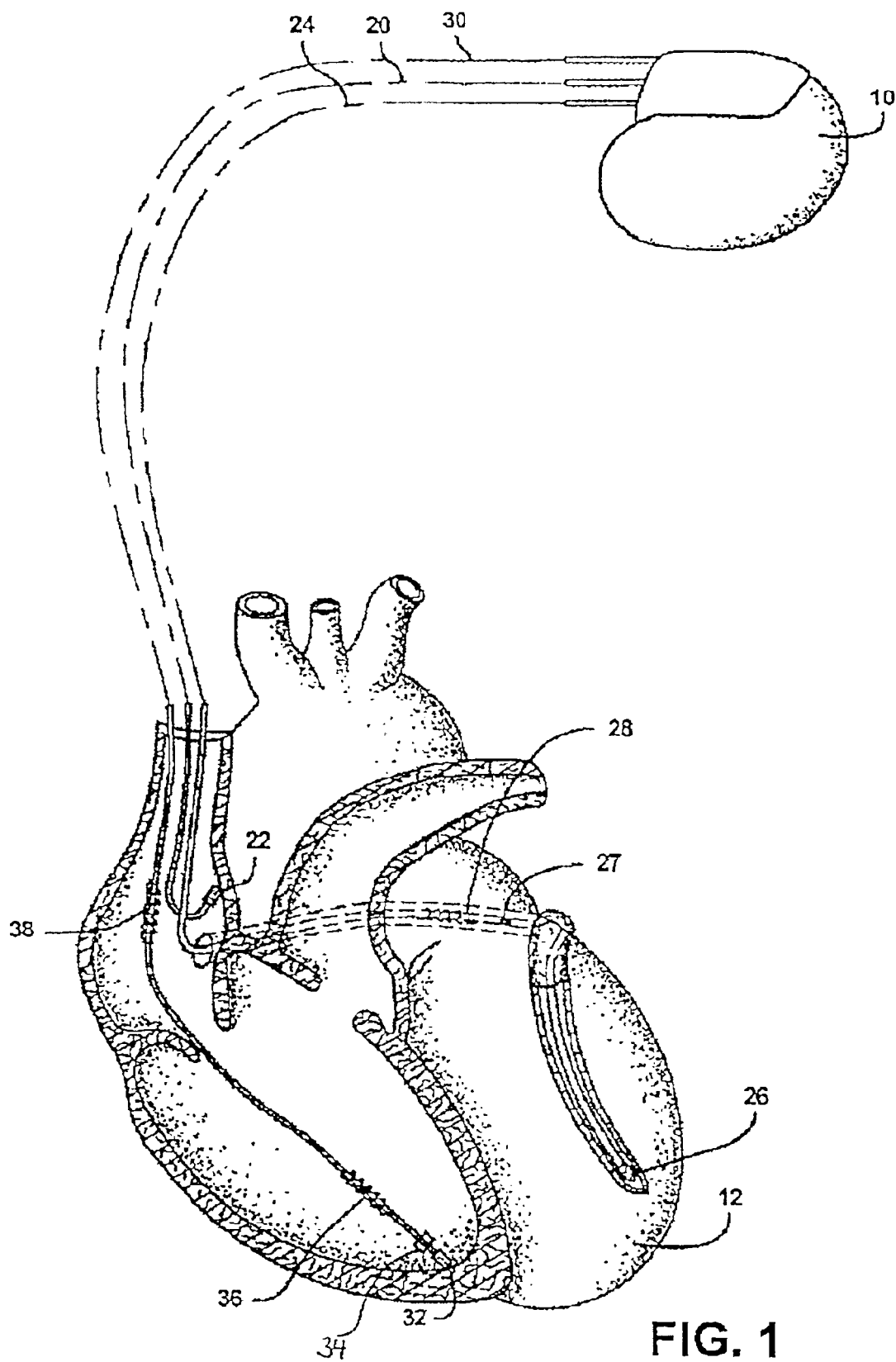
FIG. 1 is a simplified diagram illustrating an implantable stimulation device in electrical communication with at least three leads implanted into a patient's heart for delivering multi-chamber stimulation and shock therapy.

As shown in FIG. 1, there is an exemplary stimulation device 10 (also referred to as a pacing device, or a pacing apparatus) in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
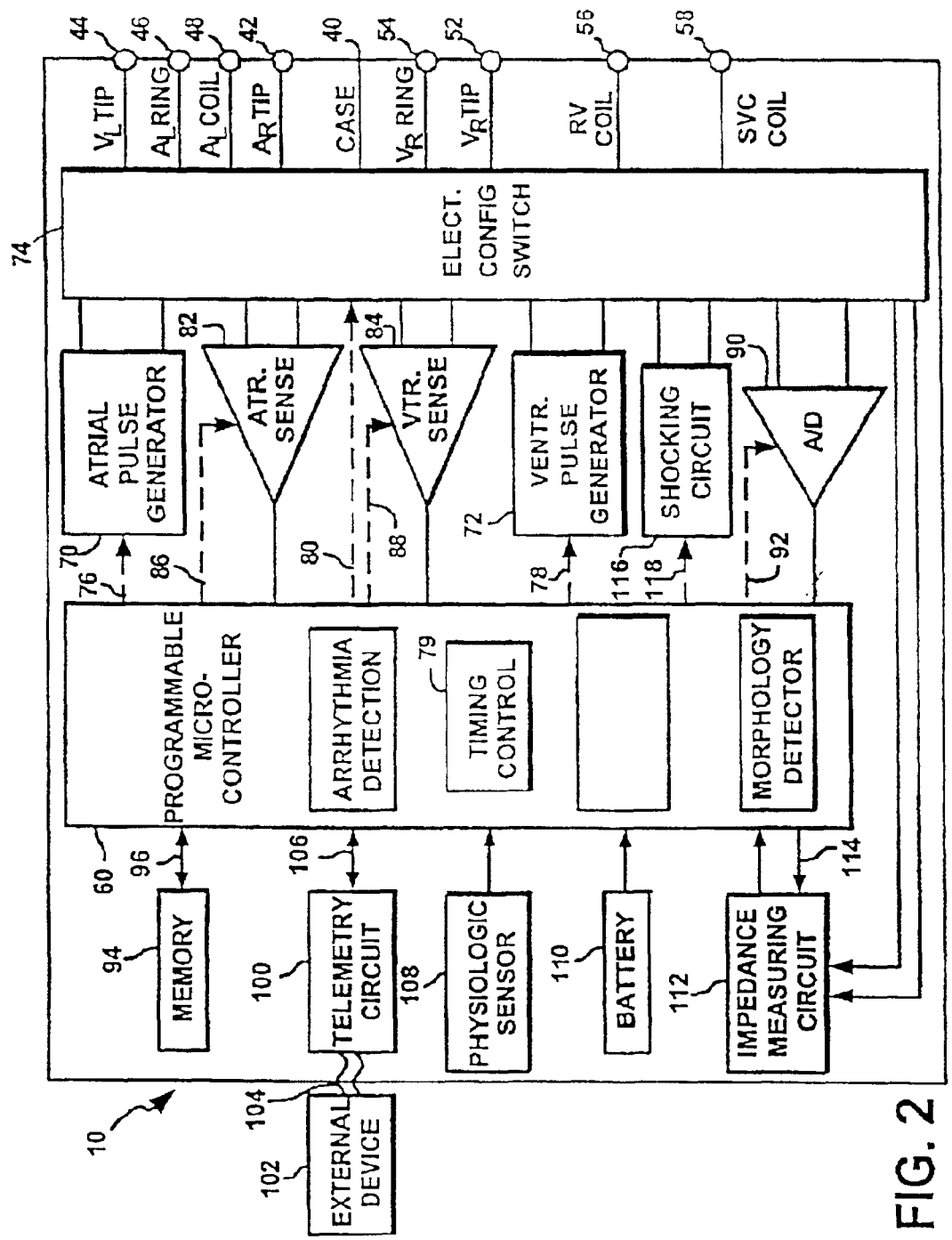
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector farther includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design of the microcontroller 60 are not critical to the present invention. Rather, any suitable microcontroller 60 can be used to carry out the functions described herein. The use of microprocessor-based control circuits for performing timing and data analysis functions are well known in the art. In specific embodiment of the present invention, the microcontroller 60 performs some or all of the steps associated with determining optimal pacing parameters in accordance with the present invention.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular (AV) delay, interventricular (RV-LV) delay, atrial interconduction (A—A) delay, ventricular interconduction (V—V) delay, and pacing rate.

The switch bank 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. Such sensing circuits, 82 and 84, can be used to determine cardiac performance values used in the present invention.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, in the appropriate chambers of the heart. The sensing circuits, 82 and 84, in turn, receive control signals over signal lines, 86 and 88, from the microcontroller 60 for purposes of measuring cardiac performance at appropriate times, and for controlling the gain, threshold, polarization charge removal circuitry (not shown), and timing of any blocking circuitry (not shown) coupled to the inputs of the sensing circuits, 82 and 86.

For arrhythmia detection, the device 10 utilizes the atrial and ventricular sensing circuits, 82 and 84, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

A feature of the present invention is the ability to sense and store a relatively large amount of data (e.g., from the data acquisition system 90). Such data can then be used for subsequent analysis to guide the programming of the device and/or to appropriately adjust pacing parameters in accordance with embodiments of the present invention.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to an external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient. Generation of Sensing Signals in an Implantable Medical Device such as a Pacemaker or ICD" (note: this relates to transfer of EGM data) (McClure et al.), which patents are hereby incorporated herein by reference.

In the preferred embodiment, the stimulation device 10 further includes a physiologic sensor 108, that can be used to detect changes in cardiac performance or changes in the physiological condition of the heart. Accordingly, the microcontroller 60 can respond by adjusting the various pacing parameters (such as rate, AV Delay, RV-LV Delay, V—V Delay, etc.) in accordance with the embodiments of the present invention. The microcontroller 60 controls adjustments of pacing parameters by, for example, controlling the stimulation pulses generated by the atrial and ventricular pulse generators, 70 and 72. While shown as being included within the stimulation device 10, it is to be understood that the physiologic sensor 108 may also be external to the stimulation device 10, yet still be implanted within or carried by the patient. More specifically, the sensor 108 can be located inside the device 10, on the surface of the device 10, in a header of the device 10, or on a lead (which can be placed inside or outside the bloodstream).

The stimulation device 10 additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement, detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized to be recognize), and pertaining exclusively to the treatment of fibrillation. Accordingly, the microcontroller 60 is capable of controlling the synchronous or asynchronous delivery of the shocking pulses.

Operation of the Present Invention

Figure 3:
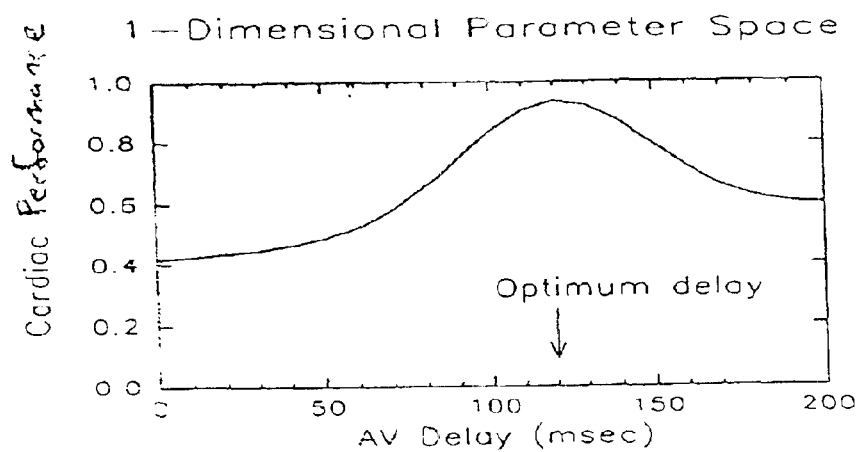
FIG. 3 is graph of a one-dimensional parameter space that illustrates cardiac performance as a function of AV delay.

As discussed above, there is a need for efficient and effective methods, systems and devices for optimizing multiple pacing parameters. This is because the number of potential pacing parameter combinations increases dramatically as the number of sites paced increases, making it potentially difficult and time consuming to determine optimal pacing parameters. This problem can be formulated in terms of an abstract mathematical space, where each dimension of the space represents an adjustable independent pacing parameter. For example, in dual-chamber pacing (e.g., right atrium and right ventricle pacing) there is a single independent parameter, the atrioventricular (AV) delay, and cardiac performance is a function of this one parameter. An example of such a one-dimensional parameter space is shown in FIG. 3.

Figure 4:
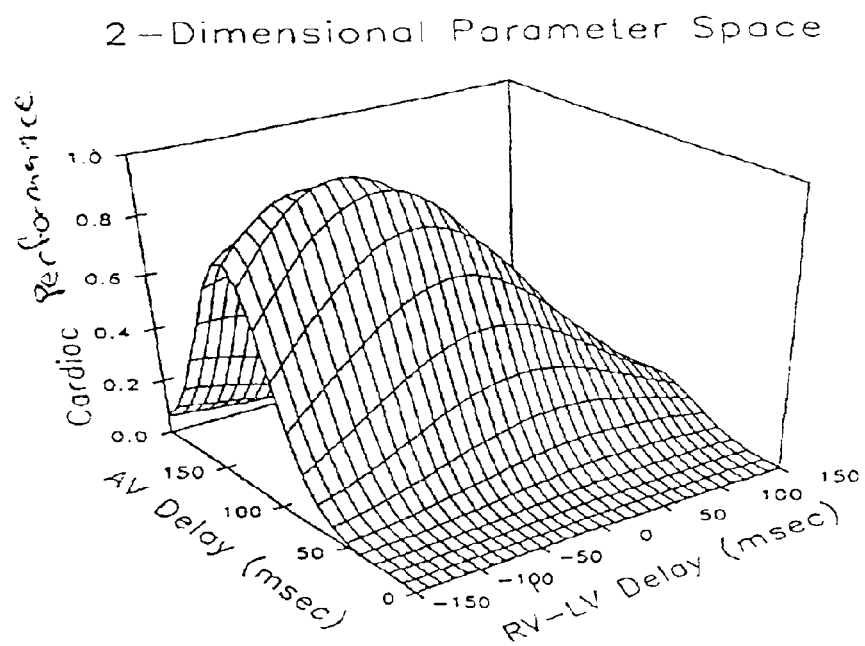
FIG. 4 is a graph of a two-dimensional parameter space that illustrates cardiac performance as a function of AV delay and RV-LV delay.

In three chamber pacing (e.g., right atrium, right ventricle and left ventricle) there are two independent parameters (AV delay and interventricular RV-LV delay), and thus, a two dimensional parameter space, with each point in the space representing a particular parameter pair. Associated with each point in space is also the cardiac performance that results from that parameter pair setting. A corresponding two-dimensional parameter space resembles a mountainous landscape that forms a three-dimensional surface over a two-dimensional latitude/longitude grid, as shown in FIG. 4. Parameter optimization in this case consists of finding the coordinates of the peak of the mountainous landscape, which represents the peak in cardiac performance.

The above discussed problem can be generalized to any number of dimensions. For example, the parameter space of a four-chamber pacemaker would have three dimensions. Similarly, pacing rate could be treated as a parameter to be optimized, which would add an additional dimension to the space.

As discussed above, an exhaustive search of parameter space becomes unworkable as the number of pacing parameters, and thus, dimensions, increases.

The present invention enables efficient and effective determinations of optimum pacing parameters when multiple parameters are being paced.

If the problem of determining optimal pacing parameters is formulated in terms of an abstract mathematical space, where each dimension of the space represents an adjustable independent pacing parameter, then the solution is finding the point in the abstract mathematical space having the maximum cardiac performance value. For example, if the problem is to find the optimal pacing parameters in dual-chamber pacing, then the solution is to find the AV delay that provides the maximum cardiac performance. Referring to the one-dimensional parameter space shown in FIG. 3, the maximum cardiac function occurs when the AV delay is 120 msec. For another example, if the problem is to find the optimal pacing parameters in three-chamber pacing, then the solution is to find the AV delay and the RV-LV delay associated with the peak of the mountainous landscape shown in FIG. 4.

Figure 5:
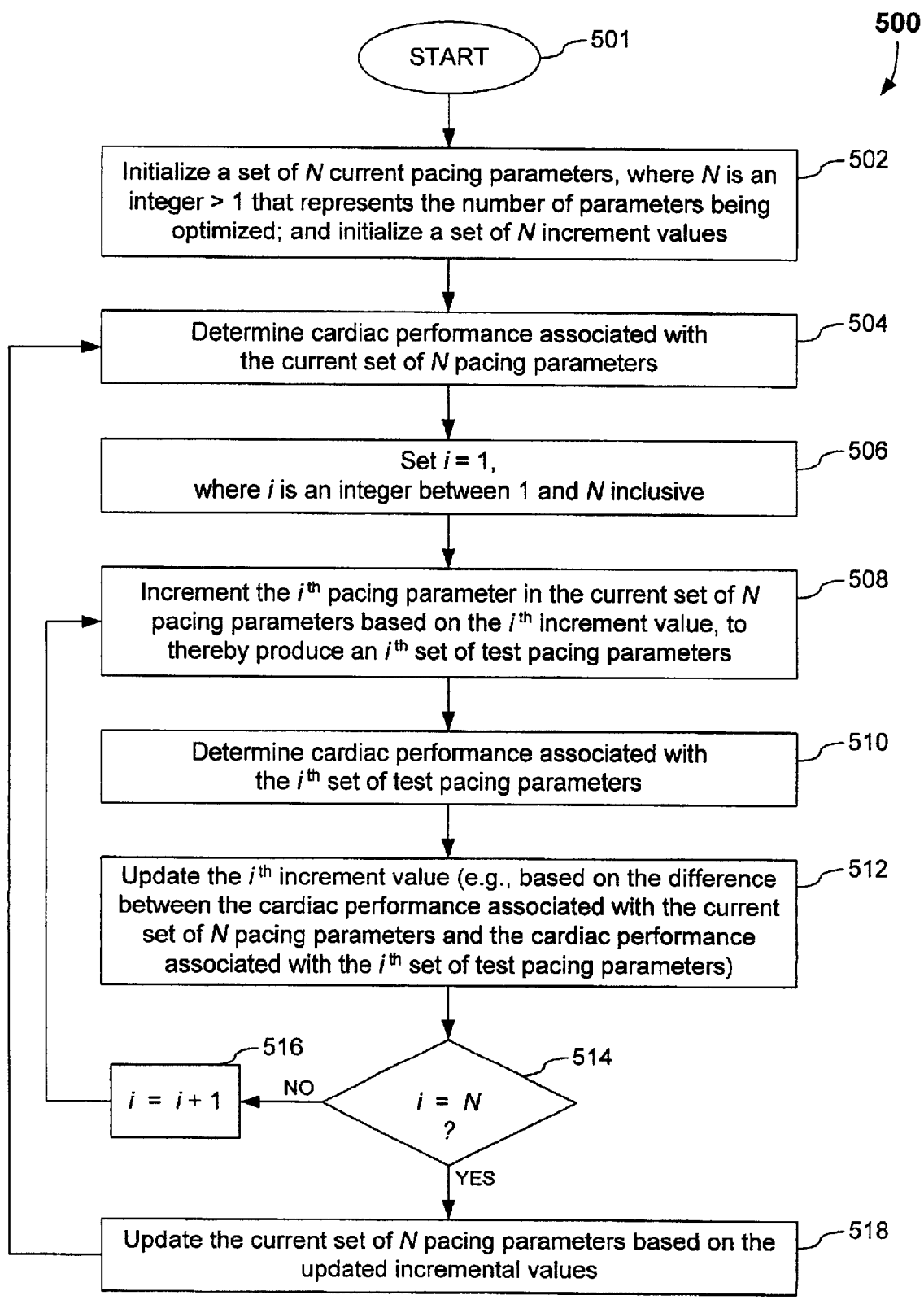
FIG. 5 is a flow chart useful for describing an overview of the operation of an embodiment of the present invention.

In FIG. 5, a flow chart is shown describing an overview of the operation and features implemented in one embodiment of the device 10. Alternatively, these features can be performed by an external device (e.g., external device 102) that communicates with the device 10. The external device 102 together and in communications with device 10 form a system. Such features can be used to efficiently and effectively determine optimum or substantially optimum pacing parameters. In this flow chart and the other flow charts described herein, the various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art can readily write such a control program based on the flow charts and other descriptions presented herein. The steps of a flowchart are collectively referred to as a method.

A first method 500 of the present invention shall now be described with reference to FIG. 5. Method 500 starts at step 501 and proceeds immediately to step 502. At step 502, a set of N current pacing parameters are initialized, wherein N represents the number of pacing parameters being optimized. (This set of N current pacing parameters is also referred to as the initial current set of pacing parameters.) For example, in a dual-chamber pacing embodiment, only one pacing parameter is being optimized (e.g., AV delay), and thus, N=1. In a three-chamber pacing embodiment, two pacing parameters are being optimized (e.g., AV delay and RV-LV delay), and thus, N=2. If four pacing parameters are being optimized, then N=3, and so on. It is noted that pacing rate is another example of a type of pacing parameter. The present invention provides the most significant improvements over conventional methods for determining optimal pacing parameters when at least two pacing parameters are being optimized (i.e., when N>1). Assuming that both AV delay and RV-LV delay are being optimized (and thus, that N=2), an example initial set of current pacing parameters is {AV delay=150 msec.; RV-LV delay=20 msec.}.

Additionally, at step 502, a set of N increment values is initialized. (This set is also referred to as the initial set of increment values.) An increment value corresponds to an amount of change (i.e., adjustment) in a parameter of the current set of pacing parameters. Continuing with the assumption that both AV delay and RV-LV delay are being optimized, an example initial set of increment values is {AV delay increment=10 msec.; RV-LV delay increment=15 msec.}.

At a next step 504, cardiac performance associated with the current set of N pacing parameters is determined. This can be accomplished by measuring cardiac performance when the heart is paced using the current set of N pacing parameters. Measurements of cardiac performance are also referred to as pulse amplitude measurements or cardiac function measurements. The pulse amplitude can be obtained in a variety of ways. For example, in one embodiment pulse amplitude (i.e., cardiac performance) is a measure of ventricular pressure, or the time-derivative of ventricular pressure, as determined by an intracavitary pressure transducer. In an alternative embodiment, vascular plethysmography is used to obtain a measure of arterial pulse amplitude. In another embodiment, heart sounds are used to obtain a measure of the strength of cardiac contraction. Other measures of cardiac performance are possible, including ultrasound to detect changes in the diameter of the aorta or other vessels during the cardiac cycle, Doppler ultrasound to detect the blood flow through arteries, cardiac motion detected by an accelerometer, ventricular volume detected by intracardiac or extracardiac impedance plethysmography. Still another measure of cardiac function is mechanical distension of arteries, which can be measured, for example, using a strain gauge, an accelerometer, or a pressure transducer. Thus, the term 'pulse amplitude' is intended to be used in the generic sense as some measure of cardiac performance. Such measures of cardiac performance can be generated, for example, on a beat-by-beat basis. Arterial pulse amplitudes, which are pulse amplitude measures derived from an increased pressure and distension of the arterial vasculature that results from a systolic pulse, may alternatively be used. Measures of arterial pulse amplitude include, for example, optical vascular plethysmography, intra- or extra-arterial pressure transduction, and ultrasound sensing. In one embodiment, step 504 can be broken into more detailed steps 702 through 716 of FIG. 7, which are discussed below.

Next, at a step 506, i is set to 1, wherein i is an integer between 1 and N (where N, as discussed above, represents the number of pacing parameters being optimized). The i represents which pacing parameter (i.e., first, second . . . Nth) is being acted upon (e.g., incremented).

At a step 508, the $i^{th}$ (i.e., first, second, etc.) pacing parameter is incremented based on a corresponding $i^{th}$ increment value, thereby producing the $i^{th}$ set of test pacing parameters. For example, when i=1, then the first pacing parameter is incremented based on a corresponding first increment value. The fist time that the $i^{th}$ pacing parameter is incremented, it is incremented based on the corresponding $i^{th}$ initial increment value in the initial set of increment values. For example, continuing with the assumption that AV delay and RV-LV delay are being optimized, and assuming that the initial set of current pacing parameters is {AV delay=150 msec.; RV-LV delay=20 msec.}, and that the initial set of increment values is {AV delay increment=10 msec.; RV-LV delay increment=15 msec.}, then the first set (i.e., when i=1) of test pacing parameters is {AV delay=160 msec.; RV-LV delay=20 msec.}. Similarly, when i=2, the second set of test parameters is {AV delay=150 msec.; RV-LV delay=35 msec.}. Notice in this embodiment, that only one of the pacing parameters, in the set of current pacing parameters, is incremented at a time.

Returning to the flow chart, at a next step 510, cardiac performance associated with the $i^{th}$ test set of pacing parameters is determined. This can be accomplished by measuring cardiac performance when the heart is paced using the $i^{th}$ test set of pacing parameters. As discussed above, measurements of cardiac performance (which are also referred to as pulse amplitude measurements, or cardiac function measurements) can be obtained in a variety of ways. Preferably, the cardiac performance associated with a test set determined at step 510, is obtained using the same procedure used to determine the cardiac performance associated with the current set of N pacing parameters at step 504. That is, if the pulse amplitude measurement associated with the current set of N pacing parameters (determined at step 504) is a measure of ventricular pressure as determined by an intracavitary pressure transducer, then the pulse amplitude measurement for a test set of pacing parameters (determined at step 510) should also be a measure of ventricular pressure as determined by an intracavitary pressure transducer.

After the cardiac performance is measured for the $i^{th}$ set of test pacing parameters, the $i^{th}$ increment value is updated at a step 512. For example, when i=1, the first pacing parameter in the current set of pacing parameters is incremented at step 508, to produce the first set of test pacing parameters. At step 510, the cardiac performance associated with the first set of test pacing parameters (i.e., the set created by incrementing the first pacing parameter of the current set of N test pacing parameters) is determined. Then, at step 512, the first increment value is updated. In an embodiment, referred to as the gradient ascent embodiment, the $i^{th}$ increment value is updated based on the difference between the cardiac performance associated with the current set of N pacing parameters and the cardiac performance associated with the $i^{th}$ set of test pacing parameters. This embodiment causes a point in parameter space to move in the uphill direction by an amount proportional to the slope of the cardiac function. This can be accomplished, for example, by updating the $i^{th}$ increment value according to the following equation:

$$\delta_1 \leftarrow k \cdot \delta_1 \cdot (P_1 - P_0)$$

where, $\delta_i$ is the $i^{th}$ increment value, k is a predetermined constant scale factor, $P_1$ is the pulse amplitude associated with $i^{th}$ set of test pacing parameters, $P_0$ is the pulse amplitude associated with current set of N pacing parameters, and $\leftarrow$ denotes replacement (i.e., updating).

It is important to note that an updated increment value can be a negative value, indicating that a pacing parameter (e.g., AV Delay) should be reduced, or possibly indicating that an order of pacing the heart should be reversed (if a particular pacing parameter can be expressed as a negative value). If a pacing parameter can be represented as a negative value, then the polarity of the pacing parameter indicates which portion of the heart is paced first. For example: an RV-LV delay of +20 msec., can indicate that the left ventricle is paced 20 msec. after the pacing of the right ventricle; and an RV-LV delay of −35 msec., can indicate that the left ventricle is paced 35 msec. prior to the pacing of the right ventricle.

Returning to the flow chart of FIG. 5, at a next step 514, there is a determination as to whether additional increment values are to be updated. This can be accomplished by determining whether i=N. For example, if i=1, and N=2 (i.e., two pacing parameters are being optimized), then the answer to step 514 is NO, and flow goes to step 516, where i is incremented by one (i.e., i=i+1), and then flow returns to step 508. During each pass through steps 508, 510 and 512: a specific (i.e., first, second, etc.) pacing parameter of the current set of N pacing parameters is incremented based on a respective increment value to produce a respective set of test pacing parameters (step 508); the cardiac performance for the set of test pacing parameters is determined (step 510); and the respective increment value is updated (step 512). It is noted that in this embodiment, the set of test pacing parameters is always the same as the current set of N pacing parameters, except that one pacing parameter (i.e., the $i^{th}$ pacing parameter) is adjusted. This allows cardiac performance to be evaluated on a parameter by parameter basis.

If the answer to step 514 is YES, indicating that each of the increment values in the set of N increment values have been updated, then flow continues to a step 518. At step 518, the current set of N pacing parameters is updated based on the updated increment values that had been determined at step 512. In other words, steps 508, 510 and 512 are performed for i=1 to N, resulting in N updated increment values. Then, at step 518, the current set of N pacing parameters is updated based on the updated increment values determined at step 512. For example, if the current set of N pacing parameters was {AV delay=150 msec.; RV-LV delay=20 msec.}, and the updated AV delay increment and updated RV-LV delay increment are, respectively, 32 msec. and −4 msec., then the updated current set of N pacing parameters is {AV delay=182 msec.; RV-LV delay=16 msec.}.

Flow then returns to step 504, where cardiac performance associated with the current set of N pacing parameters (i.e., the updated current set of pacing parameters determined in step 518) is determined. The returning of flow to step 504 shall also be referred to as the repeating of method 500 (even though steps 501 and 502 are not repeated). The updated current set of N pacing parameters produced at step 518 should provide an improved cardiac performance (measured at step 504), as compared to the cardiac performance determined during the previous pass through step 504. That is, the most recently updated current set of N pacing parameters should provide superior cardiac performance than the previous current set of N pacing parameters. In terms of parameter space, the most recently updated current set of N pacing parameters should be closer to peak point in parameter space. For example, if N=2, and the corresponding two-dimensional parameter space resembles a mountainous landscape that forms a three-dimensional surface over a two-dimensional latitude/longitude grid (as shown in FIG. 4), the point representing the most recently updated current set of N pacing parameters should be closer to the mountainous peak than the point representing the previous current set of N pacing parameters. Further, each time the current set of N pacing parameters is updated at step 518, the point in space representing the updated set should move closer and closer to the peak. This shall be illustrated in more detail below in the discussion of FIGS. 6A, 6B and 6C.

In the flow chart of FIG. 5, the method 500 for optimizing pacing parameters continues indefinitely because flow is shown as always returning to step 504 after step 518 is complete. Such a dynamic method is responsive to rapid changes in hemodynamics, as when a patient moves from supine to walking. Additionally, such a method enables continual on-the-fly pacing optimization. Further, this method for optimizing pacing parameters allows the pacing parameters to track slowly changing hemodynamic variables, such as heart rate.

The steps of method 500 need not continue indefinitely. In an alternative embodiment, the present invention is used to determine pacing parameters that will be programmed (e.g., permanently) into the pacing device 10. In such an embodiment, method 500 can be repeated a predetermined number of times (e.g., the method is repeated until step 518 is performed 10 times). In other embodiments, method 500 can be repeated until a threshold is satisfied.

In one embodiment, for example, method 500 can be repeated until a difference between the cardiac performance associated with the current set of N pacing parameters and the cardiac performance associated with the $i^{th}$ set of test pacing parameters is less than a predetermined threshold value for all i between 1 and N inclusive.

In another embodiment, where the $i^{th}$ increment value updated at step 512 is based on: A) the $i^{th}$ increment value used at step 508; and B) the difference between the cardiac performance associated with the current set of N pacing parameters (determined at step 504) and the cardiac performance associated with the $i^{th}$ set of test pacing parameters (determined in step 510), a substantially optimal current set of N pacing parameters can be found by repeating steps 504 through 518 of method 500 until each of the updated increment values (determined at step 512) is less than 2 msec. Explained in terms of parameter space, the point in parameter spaced is moved in the uphill direction by an amount proportional to the slope of the cardiac function, until the slope becomes such (i.e., relatively flat) that it is assumed that the point is near the peak. This is illustrated more detail below in the discussion of FIG. 6A.

Figure 6A:
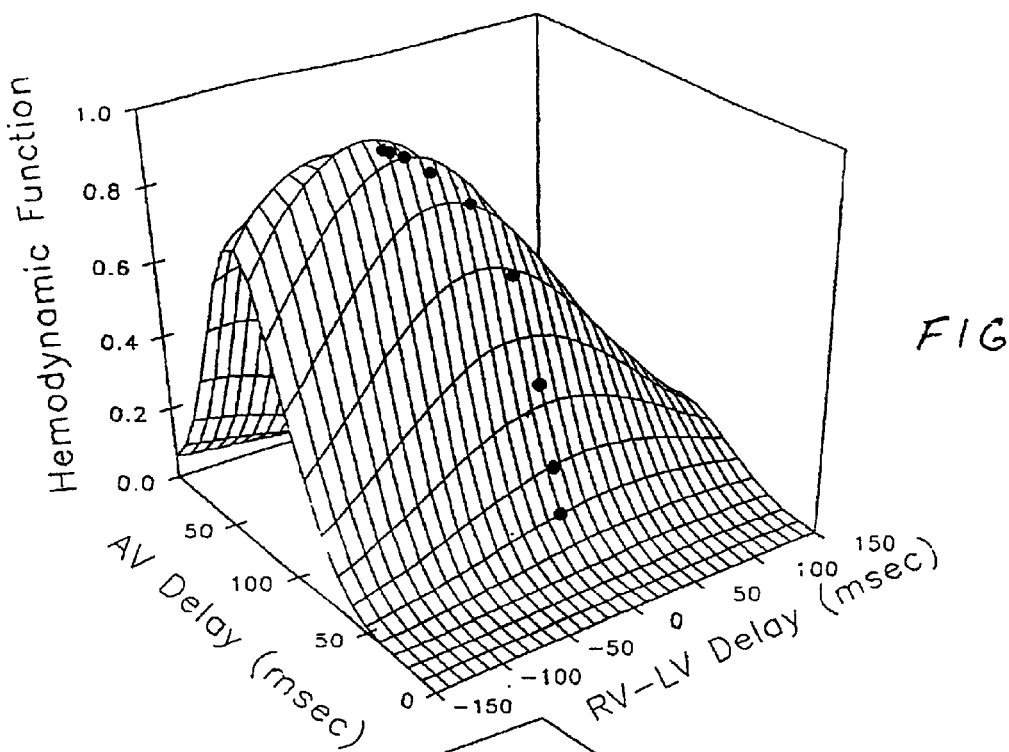
FIGS. 6A, 6B and 6C show how the two-dimensional parameter space of FIG. 4 can be efficiently and effectively searched using the present invention as described with reference to FIG. 5.
Figure 6B:
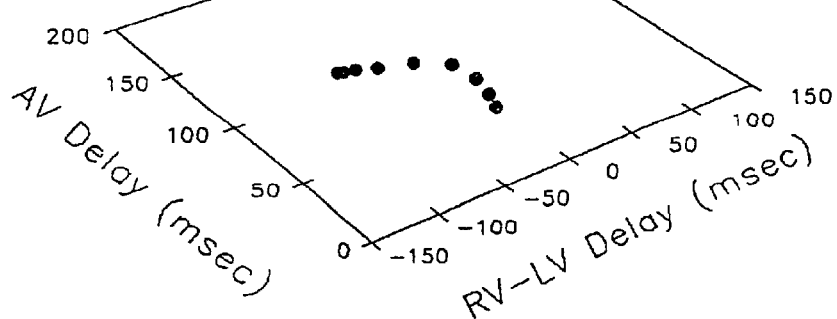
Figure 6C:
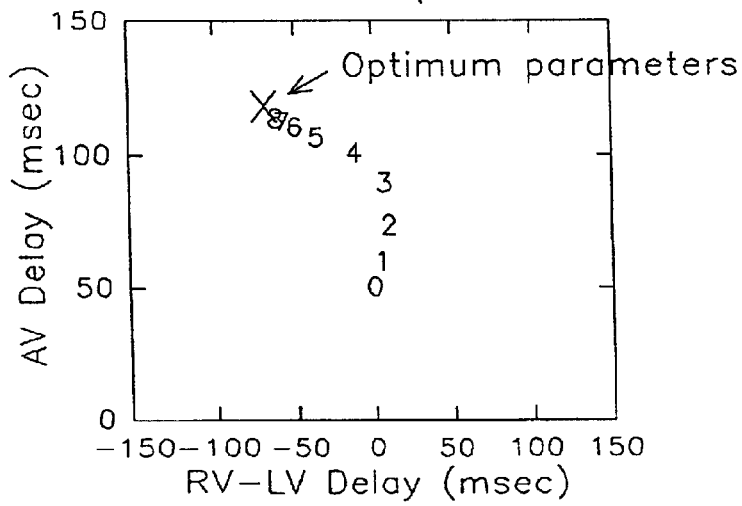

FIG. 6A shows how two pacing parameters (AV delay, and RV-LV delay) were optimized by repeating method 500 nine times. In this example, the initial current set of N pacing parameters was {AV delay=50 msec.; RV-LV delay=0 msec.} and the initial set of N increment values was {AV delay increment 10 msec.; RV-LV delay increment=5 msec.}. The mountainous landscape illustrates the cardiac function of a patient. Using conventional methods for determining optimal pacing parameters, exhaustive testing of the two-dimensional parameter space would produce the entire mountainous grid, from which the peak can be identified. However, such exhaustive testing would be computationally complex and inefficient in terms of the time and resources necessary. In contrast, as shown by the dots (X) in FIG. 6A, representing points in the mathematical space, a substantially optimum set of pacing parameters can be found by repeating method 500 nine times. FIGS. 6B and 6C help show how the point in parameter space (that represents the current set of N pacing parameters) moves rapidly toward the point the represents the optimal pacing parameters (i.e., AV delay=120, and RV-LV delay=−70).

Figure 7:
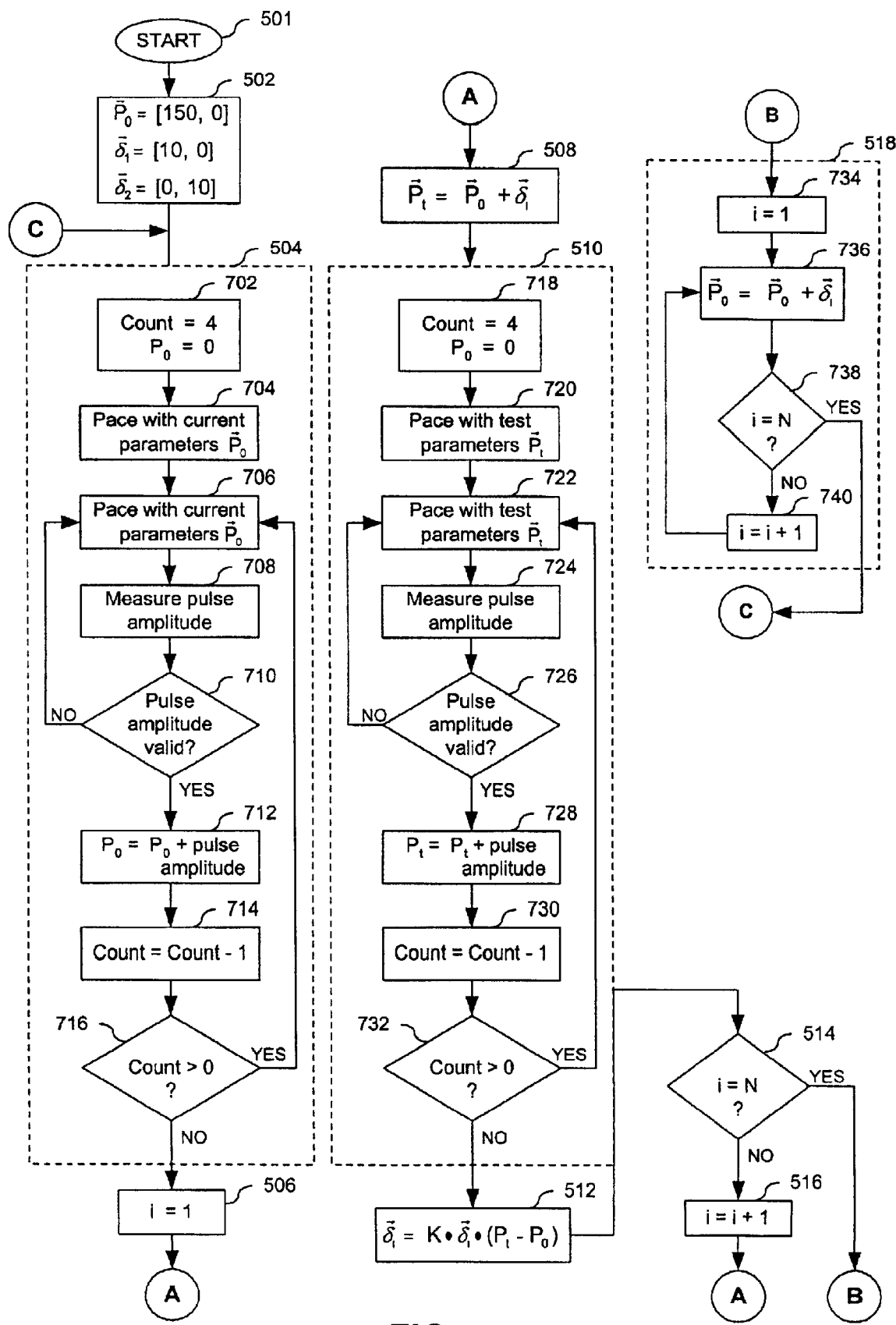
FIG. 7 is a flow chart illustrating additional details of specific steps of the flow chart of FIG. 5, according to an embodiment of the present invention.

Referring now to the flow chart of FIG. 7, one way of implementing method 500 is shown using vector notation. In this flow chart, $\vec{P}_0$ is a vector that represents the current set of N pacing parameters;

$P_0$ is the pulse amplitude associated with the current set of N pacing parameters (i.e., the pulse amplitude associated with $\vec{P}_0$);

k is a predetermined constant scale factor;

$\vec{\delta}_0$ is a vector that represents the $i^{th}$ increment value, where i is an integer between 1 and N;

$\vec{\delta}_1$ is a vector that represent the initial first increment value;

$\vec{\delta}_2$ of is a vector that represents the initial second increment value;

$\vec{P}_t$ is a vector that represents a test set of N pacing parameters; and $P_t$ is the pulse amplitude associated with a test set of pacing parameters (i.e., the pulse amplitude associated with $\vec{P}_t$).

In this embodiment, method 500 starts at step 501 and proceeds immediately to step 502. At step 502, a set of N current pacing parameters are initialized and the first and second increment values are initialized. More specifically, $\vec{P}_0$ is set to [150,0], $\vec{\delta}_1$ is set to [10,0], and $\vec{\delta}_2$ is set to [0,10], wherein, for example, the first value in each vector corresponds to AV delay, and the second value in each vector corresponds to RV-LV delay. If additional pacing parameters are being optimized, then the size of the vector is increased, as would be apparent to one of ordinary skill in the art.

Next, at step 504, cardiac performance associated with the current set of N pacing parameters is determined. In this embodiment, step 504 is broken into more detailed steps 702 through 716.

At step 702, a count is set (i.e., initialized) to a predetermined number, such as four (4), and $P_0$ is initialized to zero (0). The count represents the number of pulse amplitudes $P_0$ that will be measured when a heart is paced using the current set of N pacing parameters $\vec{P}_0$.

At a step 704, the heart is paced with the current set of N pacing parameters $\vec{P}_0$. Cardiac performance (also referred to as pulse amplitude measurements, or cardiac function measurements) is preferably not measured following this first heart beat because such a measurement could be influenced by preload conditions generated by the previous pacing of the heart. In alternative embodiments, more than the first beat are excluded from the measurement. At a step 706, the heart is again paced using the current set of N pacing parameters $\vec{P}_0$. The pulse amplitude is then measured at a step 708. The pulse amplitude can be obtained in a variety of ways, as discussed above.

At a step 710, there is a determination of whether the pulse amplitude is valid. This determination is made because pulse amplitude measurements can be corrupted by, for example, noise or motion artifacts. This step can be accomplished by analyzing a signal waveform in the time or frequency domain. For example, an arterial plethysmography waveform passed through a narrow band filter becomes positive with the arrival of a systolic pulse at the periphery. A maximum is reached approximately 100 msec. after the QRS complex. The waveform then becomes negative and achieves a minimum value within 200 msec. of the QRS complex. This information can be used to verify that a true systolic pulse has been detected, rather than noise or a motion artifact causing a false detection or degrading the measured pulse amplitude. Similarly, more complex template matching or cross correlation techniques can be used to recognize the presence of a true systolic pulse or other hemodynamic signal and to distinguish this from noise, as well as provide an estimate of the pulse amplitude. This noise detection approach can be applied to any sensor, including but not limited to pressure, flow, acceleration, acoustic, ultrasound, and oxygen and other chemical sensors. When noise is recognized to be present, a flag can be set to indicate that the measured pulse amplitude is invalid.

If the pulse amplitude is determined to be invalid (i.e., if the answer to step 710 is "NO"), then flow returns to step 706, as shown in FIG. 7. If the pulse amplitude is determined to be valid (i.e., if the answer to step 710 is "YES"), then flow continues to step 712.

At step 712, the current pulse amplitude $\vec{P}_0$ is determined according to the equation: $P_0 = P_0 + \text{pulse\_amplitude}$ (measured at step 708). In other words, at step 712 the pulse amplitudes are integrated.

At a step 714, the count is decremented according to the equation: count=count−1. At a step 716, there is a determination of whether additional pulse amplitude measurements should be made while the heart is paced using the current of N pacing parameters $\vec{P}_0$. This can be answered by determining whether the count is greater than zero.

If additional pulse amplitude measurements should be made while the heart is paced using the current set of N pacing parameters $\vec{P}_0$ (i.e., if the answer to step 716 is "YES"), then flow returns to step 706, as shown in FIG. 7. If the predetermined amount of pulse amplitude measurements have already been made while the heart is using the current set of N pacing parameters $\vec{P}_0$, then flow continues to step 506.

At step 506, i is set to 1, wherein i is an integer between 1 and N (where N, as discussed above, represents the number of pacing parameters being optimized).

At step 508, the $i^{th}$ (i.e., first, second, etc.) pacing parameter is incremented based on a corresponding $i^{th}$ increment value, thereby producing the $i^{th}$ set of test pacing parameters. In this embodiment, this is accomplished by setting $\vec{P}_t = \vec{P}_0 + \vec{\delta}_1$.

Next, at step 510, cardiac performance associated with the $i^{th}$ test set of pacing parameters is determined. In this embodiment, step 504 is broken into more detailed steps 718 through 732.

At step 718, a count is set (i.e., initialized) to a predetermined number, such as four (4), and $P_t$ is initialized to zero (0). The count represents the number of pulse amplitudes $P_t$ that will be measured when a heart is paced using the set of test pacing parameters $P_t$.

At a step 720, the heart is paced with the test set of pacing parameters $\vec{P}_t$. Cardiac performance (also referred to as pulse amplitude measurements, or cardiac function measurements) is preferably not measured following this first heart beat because such a measurement could be influenced by preload conditions generated by the previous pacing of the heart. At a step 722, the heart is again paced using the test set of pacing parameters $P_t$. The pulse amplitude is then measured at a step 724. The pulse amplitude is preferably measured in the same way it was measured at step 708.

At a step 726, there is a determination of whether the pulse amplitude is valid, as discussed above at step 710. If the pulse amplitude is determined to be invalid (i.e., if the answer to step 726 is "NO"), then flow returns to step 722. If the pulse amplitude is determined to be valid (i.e., if the answer to step 726 is "YES"), then flow continues to step 728.

At step 728, the test pulse amplitude $P_1$ is determined according to the equation: $P_t = P_1 +$ pulse_amplitude (measured at step 724). In other words, at step 728 the pulse amplitudes are integrated.

At a step 730, the count is decremented according to the equation: count=count−1. At a step 732, there is a determination of whether additional pulse amplitude measurements should be made while the heart is paced using the same set of test pacing parameters $\vec{P}_t$. This can be answered by determining whether the count is greater than zero.

If additional pulse amplitude measurements should be made while the heart is paced using the same set of test pacing parameters $\vec{P}_t$ (i.e., if the answer to step 732 is "YES"), then flow returns to step 722. If the predetermined number of pulse amplitude measurements have already been made while the heart is paced using the same set of test pacing parameters $\vec{P}_t$, then flow continues to step 512.

At step 512, the $i^{th}$ increment value is updated. In this embodiment, this is accomplished according to the equation:

$$\vec{\delta}_1 = k \cdot \vec{\delta}_1 \cdot (P_t - P_0).$$

This causes a point in parameter space to move in the uphill direction by an amount proportional to the slope of the cardiac function.

In an alternative embodiment, a fixed step size is used, thereby avoiding the need for multiplication, and reducing the computational complexity of the algorithm. For example, this can be accomplished according one of the following equations:

$$\vec{\delta}_1 = \vec{\delta}_1 \text{ if } P_t > P_0, \text{ otherwise } \vec{\delta}_1 = -\vec{\delta}_1, \text{ or}$$

$$\vec{\delta}_1 = \vec{\delta}_1 \text{ if } P_t \geq P_0, \text{ otherwise } \vec{\delta}_1 = -\vec{\delta}_1.$$

Next, at step 514, there is a determination as to whether additional increment values are to be updated. This can be accomplished by determining whether i=N. If the answer to step 514 is NO, then flow goes to step 516, wherein i is incremented by one (i.e., i=i+1), and then flow returns to step 508. During each pass through steps 508, 510 and 512, a specific (i.e., first, second, etc.) pacing parameter of the current set of N pacing parameters is incremented based on a respective increment value to produce a respective set of test pacing parameters (step 508), the cardiac performance for the set of test pacing parameters is determined (step 510), and the respective increment value is updated (step 512).

If the answer to step 514 is YES, indicating the each of the increment values in the set of N increment values have been updated, then flow continues to step 518. At step 518, the current set of N pacing parameters is updated based on the updated increment values that were determined at step 512. In this embodiment, step 518 is broken into more detailed steps 734 through 740. In steps 734 through 740, the current set of pacing parameters is updated according to the equation $\vec{P}_0 = \vec{P}_0 + \vec{\delta}_1$, for i=1 to N. In other words, steps 508, 510 and 512 are performed for i=1 to N, and then, at step 518, the current set of N pacing parameters is updated based on the updated increment values determined at step 512. Flow then returns to step 504, where cardiac performance associated with the current set of N pacing parameters (i.e., the updated current set of pacing parameters determined in step 518) is determined, as explained above in the discussion of FIG. 5.

In method 500, each increment value is independently updated prior to updating the current set of N pacing parameters. In an alternative embodiment, discussed with reference to FIG. 8, the current set of N pacing parameters is updated immediately after an increment value is updated.

Figure 8:
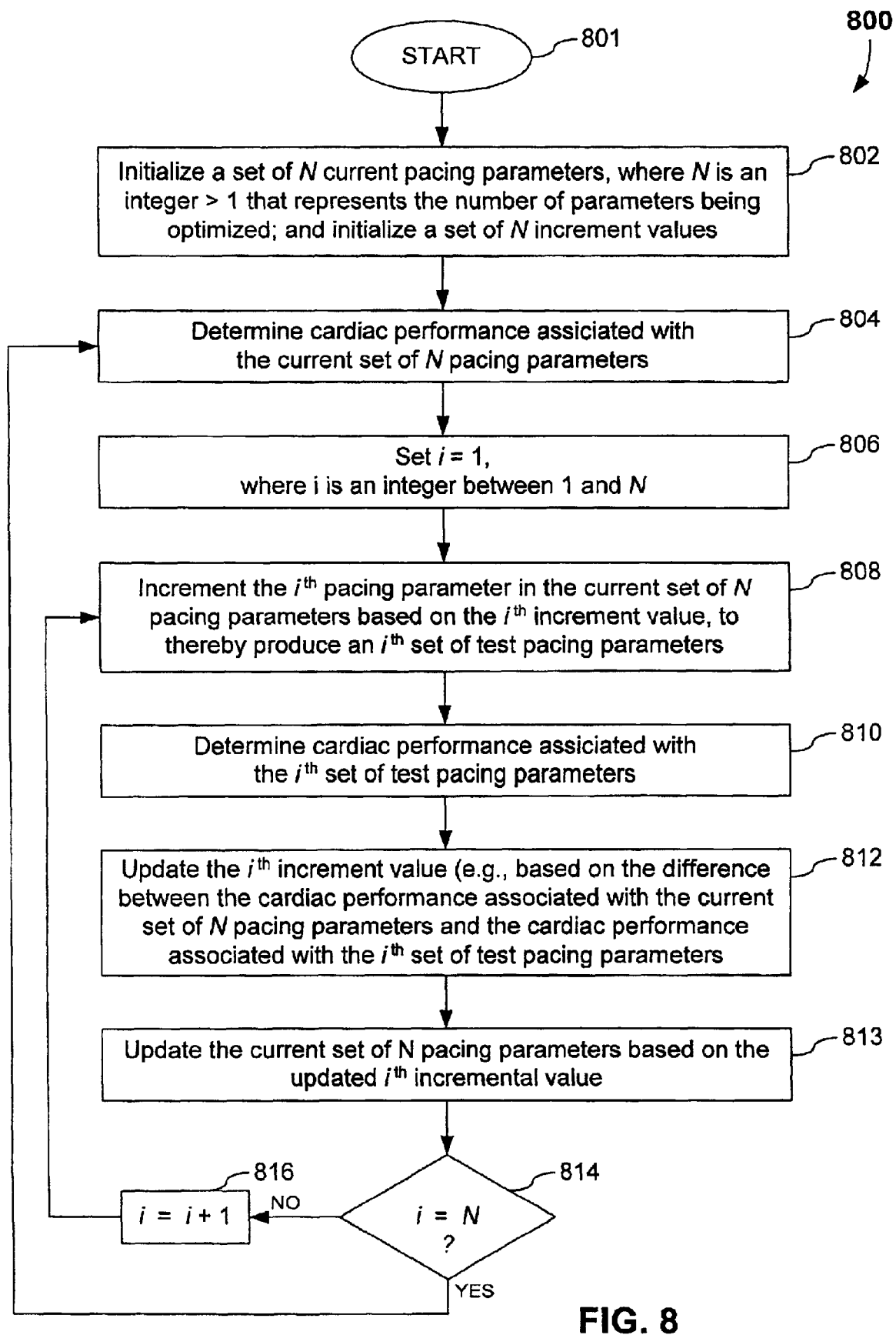
FIG. 8 is a flow chart useful for describing an overview of the operation of an alternative embodiment of the present invention.

Referring now to FIG. 8, steps 802, 804, 806, 808, 810 and 812 of a method 800 are substantially the same, respectively, as steps 502, 504, 506, 508, 510 and 512 of method 500. However, notice that at a step 813, the current set of N pacing parameters is immediately updated after an increment value is updated in step 812. This causes a point to move differently through parameter space than in method 500. More specifically, this causes the point in parameter space to always move in a direction parallel to an axis of the parameter space, as the point moves toward the peak (i.e., toward the point representing the optimal pacing parameters).

In alternative embodiments, discussed with reference to the flow chart of FIG. 9, random test parameters are used to optimize pacing parameters. The steps of the flowchart are collectively referred to as method 900. Method 900 starts at step 901 and proceeds immediately to a step 902. At step 902, which is similar to step 502 discussed above, a set of N current pacing parameters are initialized.

At a next step 904, which is similar to step 504 discussed above, cardiac performance associated with the current set of N pacing parameters is determined. Next, at a step 906, a random test set of N pacing parameters is determined. For example, if two pacing parameters are being optimized, and thus N=2, then a set including 2 random values is determined. The random values of the random set of N pacing parameters are preferably within a predefined range. For example, assume that AV delay should be within the range of 100 msec. to 175 msec., and RV-LV delay should be between −200 msec. and 200 msec. Accordingly, the determined random value corresponding to AV delay should be between 100 msec. and 175 msec. Similarly, the determined random value corresponding to RV-LV delay should be between −200 msec. and 200 msec. As discussed above, the polarity of a delay value can be used to indicate which part of the heart is paced first.

Random values can be created many different ways. For example, in one embodiment, a random value is determined by selecting one of a plurality of predefined (i.e., predetermined) numbers that have been stored. This simple embodiment would probably consume the least amount of power. Low power consumption is important if the determination is performed by an implantable device (e.g., pacing device 10). In another embodiment, a random number generator is used to generate the random values. Such a random number generator can use mathematical algorithms to generate random values. Alternatively, an element of hardware, such as a time of day clock, can be used to assist in generating random values. For example, a specific byte in the time of day clock can be sampled to produce random numbers when required. In still another embodiment, the random values can be created by performing an analog to digital conversion of a noisy channel. Of course, the use of other devices and/or methods for generating random values are within the spirit and scope of the present invention. Additionally, software, hardware, or combination of software and hardware can be used to generate the random values. For a more complete description of random number generation, see Chapters 7 and 10 of "Numerical Recipes in C, The Art of Scientific Computing, Second Edition" by Press et al., Cambridge University Press (1999), which are hereby incorporated herein by reference.

Returning to the flow chart, at a next step 908, the cardiac performance associated with the test set of pacing parameters is determined, preferably, in the same way it was measured in step 904.

Finally, at a step 910, if the cardiac performance associated with the test set of pacing parameters is better than the cardiac performance associated with the current set of N pacing parameters, then the current set of N pacing parameters is replaced with the test set of pacing parameters.

Flow then returns to step 904, where cardiac performance associated with the current set of N pacing parameters (which is the same as the previous current set of pacing parameters, unless the current set of N pacing parameters was replaced with the test set of N pacing parameters at step 910). In this manner, method 900 continually replaces the current set of N pacing parameters with any test set of pacing parameters that is determined to have produced better cardiac performance.

Figure 9:
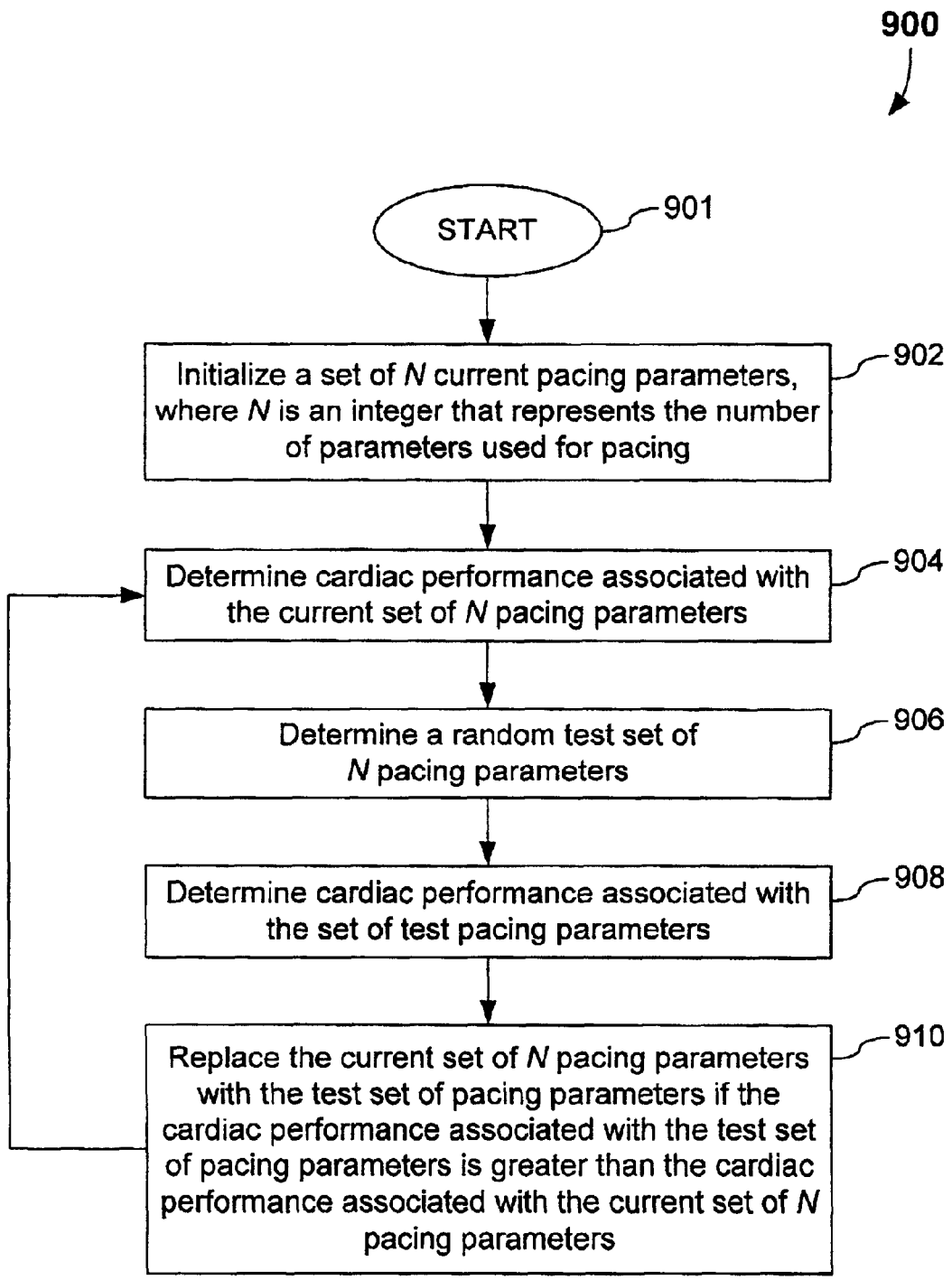
FIG. 9 is a flow chart useful for describing an overview of the operation of additional alternative embodiments of the present invention.

Method 900 can continue indefinitely, as shown in FIG. 9. Such a method is responsive to rapid changes in hemodynamics, as when a patient moves from supine to walking. Additionally, such a method enables continual on-the-fly pacing optimization. Further, this method for optimizing pacing parameters allows the pacing parameters to track slowly changing hemodynamic variables, such as heart rate.

The steps of method 900 need not continue indefinity. In an alternative embodiment, the present invention is used to determine pacing parameters that will be programmed (e.g., permanently) into a pacing device. In such an embodiment, method 900 can be repeated a predetermined number of times (e.g., the method is repeated until step 904 is performed 10 times). In another embodiment, method 900 can be repeated until a threshold is satisfied. For example, in one embodiment steps 904 through 910 are repeated until, for a predetermined number of consecutive times (e.g., 10 consecutive times), the cardiac performance associated with the test set of pacing parameters is not better than the cardiac performance associated with the current set of N pacing parameters. Stated another way, steps 904 through 910 can be repeated until there is no replacement of the current set of N parameters with the test set of N pacing parameters at step 910, ten consecutive times. If after X consecutive iterations of step 910, the current set of N parameters is not replaced, then the current set of N parameters is likely to be within the top 1/X optimal sets of N pacing parameters. For example, if after 10 consecutive iterations of step 910 (i.e., X=10), the current set of N parameters is not replaced, then the current set of N pacing parameters is likely to be within the top 10% (i.e., 1/10=0.10=10%) of pacing parameters.

In one embodiment, the range from which random values are selected is shrunk (i.e., made smaller) each time the current set of N pacing parameters is replaced with the test set of N pacing parameters at step 910. This should help accelerate finding an optimum set of N pacing parameters.

Figure 10:
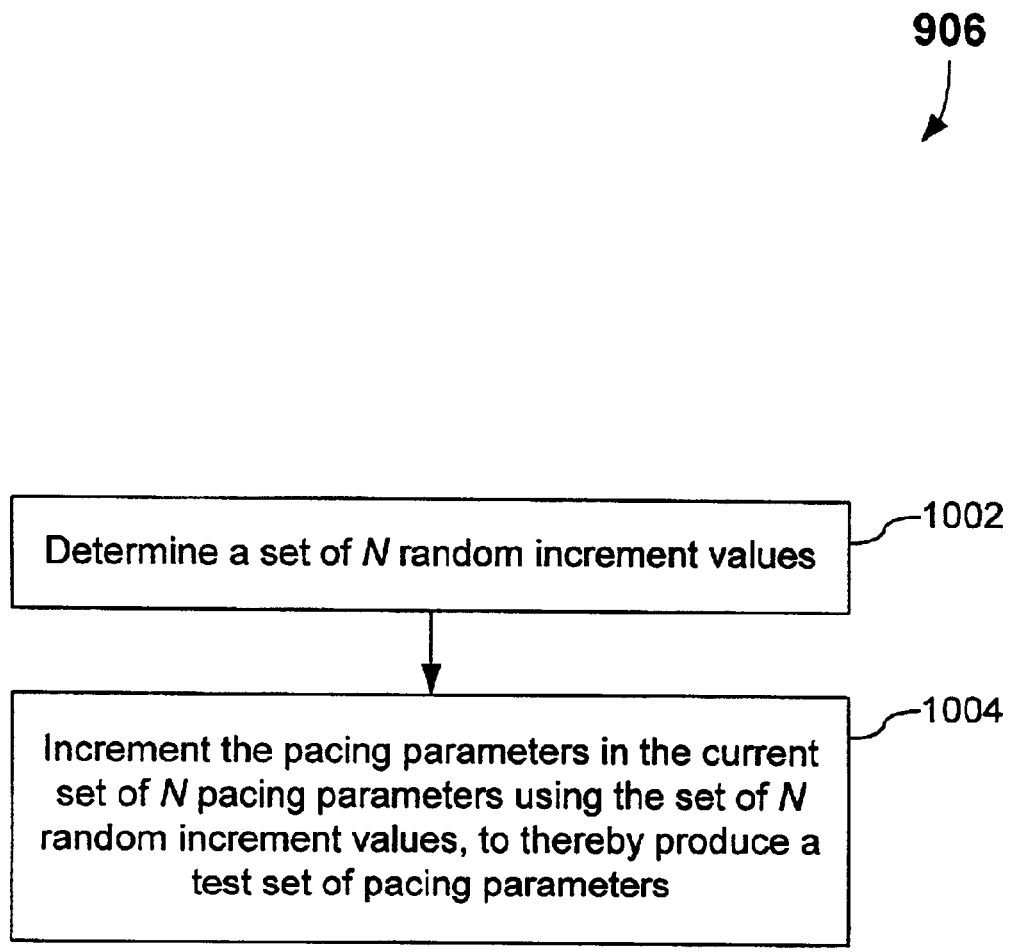
FIG. 10 is a flow chart illustrating additional details of a specific step of the flow chart of FIG. 9, according to an embodiment of the present invention.

It may be possible that sudden shifts in pacing parameters could have deleterious effects on patients. Accordingly, it may be desirable to limit the random searching to a small range around the currently best known pacing parameters. This will also speed convergence. One way this can be accomplished is described with reference to FIG. 10. More specifically, in FIG. 10, step 906 is broken into steps 1002 and 1004. At a step 1002, a set of N random increment values are determined. In one embodiment, the random increment values are within a predefined range, such that appropriate test sets of pacing parameters are produced. For example, assume the initial current set of pacing parameters is {AV delay=150 msec.; RV-LV delay=20 msec.}, and assume that AV delay should be within the range of 100 msec. to 175 msec., and RV-LV delay should be between −200 msec. and 200 msec. An example range of random values for use as an AV delay increment value may be between −10 msec. and 10 msec., and an example range of random values for use as an RV-LV increment value may be between −20 msec. and 20 msec.

After a set of N random increment values are determined at step 1002, then, at a step 1004, the current set of N pacing parameters is incremented using the set of N random increment values, thereby producing the random test set of pacing parameters. In this embodiment, the cardiac performance associated with the random set of pacing parameters determined at step 1004 is then determined (i.e., at step 908) and method 900 is otherwise the same as described above in the discussion of FIG. 9. The method described with reference to FIG. 10 has the advantage of avoiding sudden dramatic shifts in pacing parameters, which could have deleterious effects on patients.

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention.

Embodiments of the present invention discussed above have been primarily described as methods with reference to flow charts. The present invention is also directed to devices (also referred to as apparatuses) that perform the features discussed above. For example, the present invention is also directed to a microprocessor (e.g., microprocessor 60) that performs the features of the present invention. Additionally, the present invention is also directed to an implantable device (e.g., pacing device 10) that includes a microprocessor for performing such features. Further, the present invention is also directed to systems that perform the features discussed above. Such a system can be, for example, an external processor in communications with a microprocessor of an implantable device. These examples are not meant as limitations.

Advantages of the Present Invention

There are a number of reasons why the present invention is invaluable, some of which are discussed below.

The present invention enables automatic optimization of pacing parameters, thereby sparing electrophysiologists the time and effort of manually searching the parameter space for optimal settings. Further, by shortening the procedure, the present invention can be used to reduce risk to patients.

Different disease states require different parameter settings. For example, desynchronizing ventricular contraction improves cardiac performance in Hypertrophic Obstructive Cardiomyopathy, while in Dilated Cardiomyopathy cardiac performance is improved with synchrony. The embodiments of the present invention are general and adaptable, enabling adaption to either example.

Rapid parameter adjustment is necessary for on-the-fly pacing parameter optimization that allows an apparatus to respond to rapid changes in hemodynamics, as when a patient moves from supine to walking. Methods of parameter adjustment that require more than a minute or two preclude on-the-fly parameter optimization. The embodiments of the present invention are efficient and effective enough to allow for on-the-fly pacing optimization.

For patients whose baseline cardiac function is so compromised that pacing intervention is necessary, it is very important that the optimal parameter values are used. Ineffective approaches for determining pacing parameters may force compromises in the pacing parameters that are selected. The embodiments of the present invention enable optimal cardiac function to be obtained.

Further, the embodiments of the present invention allow the pacing parameters to track slowly changing hemodynamic variables, such as heart rate, blood pressure, and intrinsic contractility.

What is claimed is:

1. A method for improving cardiac performance associated with a current set of N pacing parameters by adjusting the N cardiac pacing parameters, where N is an integer greater than one, the method comprising the steps of:
   (a) determining cardiac performance associated with the current set of N pacing parameters;
   (b) repeating steps (c) through (e) for i=one to N, where i represents which of the N pacing parameter is being adjusted;
   (c) in renting an $i^{th}$ pacing parameter in the current set of N pacing parameters based on a corresponding $i^{th}$ increment value to thereby produce an $i^{th}$ set of test pacing parameters;
   (d) determining a cardiac performance associated with the $i^{th}$ set of test pacing parameters;
   (e) updating the $i^{th}$ increment value based on the cardiac performance associated with the $i^{th}$ set of test pacing parameters; and
   (f) updating the current set of N pacing parameters based on the updated increment values determined in step (e).

2. The method of claim 1, wherein step (e) comprises the step of updating the $i^{th}$ increment value based on the difference between the cardiac performance associated with the current set of N pacing parameters and the cardiac performance associated with the $i^{th}$ set of test pacing parameters.

3. The method of claim 1, wherein step (e) comprises the step of updating the $i^{th}$ increment value based on:
   the $i^{th}$ increment value used in stop (c), and
   the difference between the cardiac performance associated with the current set of N pacing parameters and the cardiac performance associated with the $i^{th}$ set of test pacing parameters.

4. The method of claim 3, wherein step (e) comprises the step of updating the $i^{th}$ increment value based on the equation:

$$\delta_i \leftarrow k \cdot \delta_i \cdot (P_t - P_0)$$

where,
   $\delta_1$ is the $i^{th}$ increment value,
   k is a predetermined constant scale factor,
   $P_t$ is a measure of the cardiac performance associated with $i^{th}$ set of test pacing parameters as determined in step (d),
   $P_0$ is a measure of the cardiac performance associated with the current set of N pacing parameters as determined in step (a), and
   ← denotes replacement.

5. The method of claim 1, wherein step (e) comprises the step of updating the $i^{th}$ increment value based on one of the following equations:

$$\delta_i \leftarrow \delta_i \text{ if } P_1 > P_0, \text{ otherwise } \delta_i \leftarrow -\delta_i, \text{ and} \quad (1)$$

$$\delta_i \leftarrow \delta_i \text{ if } P_1 \geq P_0, \text{ otherwise } \delta_i \leftarrow -\delta_i, \quad (2)$$

where,
   $\delta_i$ is the $i^{th}$ increment value,
   $P_t$ is a measure of the cardiac performance associated with $i^{th}$ set of test pacing parameters as determined in step (d),
   $P_0$ is a measure of the cardiac performance associated with the current set of N pacing parameters as determined in step (a), and
   ← denotes replacement.

6. The method of claim 1, further comprising the step of:
   (g) repeating steps (a) through (f).

7. The method of claim 1, further comprising the step of:
   (g) repeating steps (a) through (f) until each of the updated increment values determined in step (e) is less than a predetermined threshold value.

8. The method of claim 1, further comprising the step of:
   (g) repeating steps (a) through (f) until a difference between the cardiac performance associated with the current set of N pacing parameters and the cardiac performance associated with the $i^{th}$ set of test pacing parameters is less than a predetermined threshold value for all i between 1 and N inclusive.

9. A method for improving cardiac performance associated with a current set of N pacing parameters by adjusting the N cardiac pacing parameters, where N is an integer greater than 1, the method comprising the steps of:
   (a) determining cardiac performance associated with the current set of N pacing parameters;
   (b) incrementing the $i^{th}$ pacing parameter in the current set of N pacing parameters based on an $i^{th}$ increment value, to thereby produce an $i^{th}$ set of test pacing parameters, wherein i is an integer between 1 and N inclusive;
   (c) determining cardiac performance associated with the $i^{th}$ set of test paving parameters;
   (d) updating the $i^{th}$ increment value;
   (a) updating the current set of N pacing parameters based on the updated $i^{th}$ increment value determined in step (d); and
   (f) repeating steps (a) through (e) for all N pacing parameters.

10. The method of claim 9, wherein step (d) comprises the step of updating the $i^{th}$ increment value bay on the difference between the cardiac performance associated with the current set of N pacing parameters and the cardiac performance associated with the $i^{th}$ set of test pacing parameters.

11. The method of claim 9, wherein step (d) comprises the step of updating the $i^{th}$ increment value based on:
   the $i^{th}$ increment value used in step (c), and
   the difference between the cardiac performance associated with the current set of N pacing parameters and the cardiac performance associated with the $i^{th}$ set of test pacing parameters.

12. The method of claim 11, wherein step (d) comprises the step of updating the $i^{th}$ increment value bused on the equation:

$$\delta_i \leftarrow k \cdot \delta_i \cdot (P_1 - P_0)$$

where,
   $\delta_1$ is the $i^{th}$ increment value,
   k is a predetermined constant scale factor,
   $P_1$ is a measure of the cardiac performance associated with $i^{th}$ set of test pacing parameters as determined in step (d),
   $P_0$ is a measure of the cardiac performance associated with the current set of N pacing parameters as determined in step (a), and
   $\leftarrow$ denotes replacement.

13. The method of claim 9, wherein step (d) comprises the step of updating the $i^{th}$ increment value based on one of the following equations:

$$\delta_i \leftarrow \delta_i \text{ if } P_1 > P_0, \text{ otherwise } \delta_i \leftarrow -\delta_i, \text{ and} \quad (1)$$

$$\delta_i \leftarrow \delta_i \text{ if } P_1 \geq P_0, \text{ otherwise } \delta_i \leftarrow -\delta_i, \quad (2)$$

where,
   $\delta_i$ is the $i^{th}$ increment value,
   $P_1$ is a measure of the cardiac performance associated with $i^{th}$ set of test pacing parameters as determined in step (d),
   $P_0$ is a measure of the cardiac performance associated with the current set of N pacing parameters as determined in step (a), and
   $\leftarrow$ denotes replacement.

14. The method of claim 9, further comprising the step of:
   (g) repeating steps (a) through (f).

15. The method of claim 9, further comprising the step of:
   (g) repeating steps (a) through (f) until each of the updated increment values determined in step (d) is less than a predetermined threshold value.

16. The method of claim 9, further comprising die step of:
   (g) repeating steps (a) through (f) until a difference between the cardiac performance associated with the current set of N pacing parameters and the cardiac performance associated with the $i^{th}$ set of test pacing parameters is less than a predetermined threshold value for all i between 1 and N inclusive.

17. A method for improving cardiac performance associated with a current set of N pacing parameters by adjusting the N cardiac pacing parameters, where N is an integer, the method comprising the steps of:
   (a) determining cardiac performance associated with the current set of N pacing parameters;
   (b) determining a random test set of N pacing parameters;
   (c) determining cardiac performance associated with the test set of N pacing parameters; and
   (d) replacing the current set of N pacing parameters with the test set of N pacing parameters if the cardiac performance associated with the test set of N pacing parameters is greater than the cardiac performance associated with the current set of N pacing parameters.

18. The method of claim 17, wherein step (b) comprises selecting N values from a plurality of predefined values, the selected N values comprising the random test set of N pacing parameters.

19. The method of claim 17, further comprising the step of:
   (f) repeating steps (a) through (e).

20. The method of claim 17, further comprising the step of:
   (f) repeating steps (a) through (e) until, for a predetermined number of consecutive times, the cardiac performance associated with the test set of N pacing parameters is not greater than the cardiac performance associated with the current set of N pacing parameters.

21. The method of claim 17, wherein step (b) comprises the steps of:
   i. determining a set of N random increment values; and
   ii. incrementing the pacing parameters in the current set of N pacing parameters using the set of N random increment values, to thereby produce the random test set of N pacing parameters.

22. The method of claim 21, wherein step (b)i. comprises selecting N values from a plurality of predefined values, the selected N values comprising the set of N random increment values.

23. The method of claim 21, further comprising the step of:
   (f) repeating steps (a) through (c).

24. The method of claim 21, further comprising the step of:
   (f) repeating steps (a) through (e) until, for a predetermined number of consecutive times, the cardiac performance associated with the test set of N pacing parameters is not greater than the cardiac performance associated with the current set of N pacing parameters
   ii. incrementing the pacing parameters in the current set of N pacing parameters using the set of N random increment values, to thereby produce the random test set of N pacing parameters.

* * * * *

UNITED STATES PATENT AND TRADEMARK OFFICE
CERTIFICATE OF CORRECTION

| | |
|---|---|
| PATENT NO. | : 6,792,310 B1 |
| DATED | : September 14, 2004 |
| INVENTOR(S) | : Turcott et al. |

It is certified that error appears in the above-identified patent and that said Letters Patent is hereby corrected as shown below:

<u>Column 22,</u>
Line 1, subheading (c), please replace "in renting" with -- incrementing --.

Signed and Sealed this

Twenty-ninth Day of March, 2005

JON W. DUDAS
*Director of the United States Patent and Trademark Office*